(12) United States Patent
Gharpure et al.

(10) Patent No.: US 7,777,056 B2
(45) Date of Patent: Aug. 17, 2010

(54) METHOD FOR MANUFACTURE OF 4-HYDROXY PYRAN-2-ONE DERIVATIVES

(75) Inventors: Milind Moreshwar Gharpure, Pune (IN); Swapnil Panditrao Sonawane, Pune (IN); Srihari Shivaji Mane, Pune (IN); Rajendra Dagesing Mahale, Pune (IN)

(73) Assignee: Lupin Ltd., Mumbai (IN)

( * ) Notice: Subject to any disclaimer, the term of this patent is extended or adjusted under 35 U.S.C. 154(b) by 690 days.

(21) Appl. No.: 11/547,533

(22) PCT Filed: Mar. 30, 2004

(86) PCT No.: PCT/IN2004/000075

§ 371 (c)(1),
(2), (4) Date: Jul. 11, 2007

(87) PCT Pub. No.: WO2005/095374

PCT Pub. Date: Oct. 13, 2005

(65) Prior Publication Data

US 2008/0269508 A1    Oct. 30, 2008

(51) Int. Cl.
*C07D 311/02* (2006.01)
(52) U.S. Cl. ..................................................... 549/283
(58) Field of Classification Search ................. 549/283
See application file for complete search history.

(56) References Cited

U.S. PATENT DOCUMENTS

| 4,231,938 A | 11/1980 | Monaghan et al. |
| 4,346,227 A | 8/1982 | Terahara et al. |
| 4,444,784 A | 4/1984 | Hoffman et al. |
| 4,739,073 A | 4/1988 | Kathawala |
| 4,820,850 A | 4/1989 | Verhoeven et al. |
| 4,916,239 A * | 4/1990 | Treiber ........................ 549/292 |
| 5,273,995 A | 12/1993 | Roth |
| 5,712,130 A | 1/1998 | Hajko et al. |
| 5,917,058 A | 6/1999 | Kumar et al. |
| 5,939,564 A | 8/1999 | Kumar et al. |
| 6,380,401 B1 * | 4/2002 | McManus et al. ............ 549/292 |
| 6,472,542 B1 * | 10/2002 | Galeazzi et al. ............. 549/292 |
| 6,562,984 B2 * | 5/2003 | Peters et al. ................ 549/292 |
| 6,649,775 B2 | 11/2003 | Lee et al. |
| 2003/0109723 A1 | 6/2003 | Lee et al. |

FOREIGN PATENT DOCUMENTS

| EP | 0 877 742 B1 | 8/2001 |
| EP | 1 316 552 A1 | 6/2003 |
| WO | 97/20834 | 12/1997 |
| WO | 98/50572 | 11/1998 |
| WO | 01/44144 A2 | 6/2001 |
| WO | 01/44144 A3 | 6/2001 |
| WO | 02/00615 A2 | 1/2002 |
| WO | 02/094803 A1 | 11/2002 |
| WO | 02/094804 A1 | 11/2002 |

* cited by examiner

*Primary Examiner*—D. Margaret Seaman
*Assistant Examiner*—Nizal S Chandrakumar
(74) *Attorney, Agent, or Firm*—Merchant & Gould P.C.

(57) ABSTRACT

A process for preparation of 4-hydroxy-pyran-2-one derivative of formula (I),

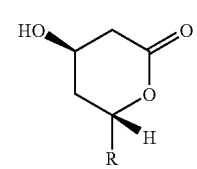

(I)

wherein R is,

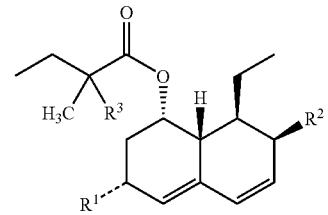

and wherein $R^1$ and $R^2$ are methyl and $R^3$ is hydrogen or methyl,
comprising the steps of,
heating a compound of formula (II),

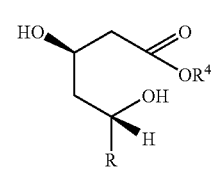

(II)

wherein R is as defined before, and $R^4$ is hydrogen, $NH_4^+$ or an alkali metal,
in a solvent mixture consisting of an aromatic hydrocarbon and a ketone in an inert atmosphere at a temperature of between 60° C. to 92° C. in the absence or presence of orthophosphoric acid or its alkali dihydrogen salts or alkali hydrogen salts of a dibasic acid, followed by optional neutralization of the reaction mixture with an organic base and obtaining compound of formula (I) in high purity and substantially free of impurities through a step of isolation and crystallization. The process leads to formation of derivatives of formula I in high purity with dimmer impurity (III) less than 0.1% and anhydro impurity (IV) below 0.15%.

15 Claims, No Drawings

METHOD FOR MANUFACTURE OF 4-HYDROXY PYRAN-2-ONE DERIVATIVES

FIELD OF INVENTION

The present invention relates, to an improved method for manufacture of 4-hydroxy-pyran-2-one derivative of formula (I) from the corresponding 3,5-dihydroxy pentanoic acid derivative of formula (II) in high purity.

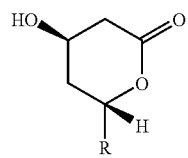

BACKGROUND OF THE INVENTION

HMG-CoA reductase inhibitors are valuable anti-hypercholesterolemic drugs, which inhibit the biosynthesis of cholesterol by competitively inhibiting 3-hydroxy-3-methylglutaryl-coenzyme A reductase (HMG-CoA reductase) and leading to a reduction in the rate of formation of cholesterol in the human body.

Therapeutically and commercially valuable anti-hypercholestoremic drugs include atorvastatin, lovastatin, mevastatin, pravastatin, simvastatin, rosuvastatin, fluvastatin etc. which can be represented by the general structural formula (I), wherein,

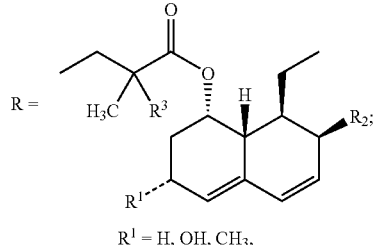

$R^1$ = H, OH, $CH_3$,
$R^2$ = $CH_3$,
$R^3$ = H, $CH_3$

I(a): $R^1 = R^2 = CH_3$; $R^3 = H$
I(b): $R^1 = R^2 = CH_3$; $R^3 = CH_3$
I(c): $R^1 = R^3 = H$; $R^2 = CH_3$

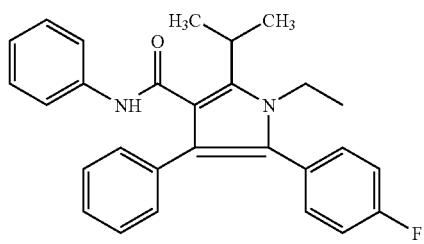

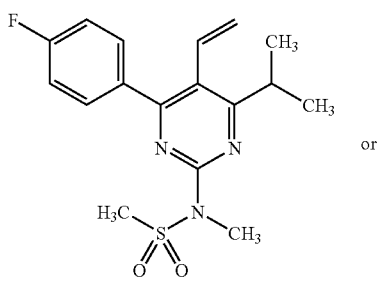

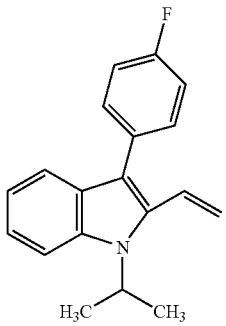

While, some of these drugs like lovastatin, simvastatin and mevastatin have a 4-hydroxy pyran-2-one structure in the cyclised lactone form, in others the 4-hydroxy pyran-2-one substituent is present in the open chain form i.e. as 3,5-dihydroxy pentanoic acid derivative (II).

Invariably, there is a common step of lactonisation in all the statin compounds, involving lactonisation of the corresponding 3,5-dihydroxy pentanoic acid derivative (II) to the 4-hydroxy pyran-2-one derivative of formula (I).

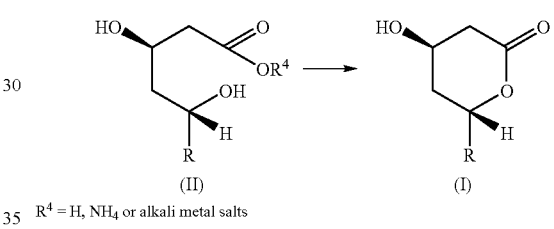

$R^4$ = H, $NH_4$ or alkali metal salts

For example, lovastatin (Ia) is prepared by lactonisation of the 3,5-dihydroxy pentanoic acid derivative (II) to (Ia) either by heating in an organic solvent or in the presence of an acid catalyst. The former, viz. mevinolinic acid, is obtained from a fermentation broth containing *Asperigillus Terreus*.

Similarly, simvastatin (Ib), a structural analogue of lovastatin, having an additional methyl group in the 2-methyl butyryl substituent is synthesized from lovastatin.

The final step in the synthesis of lovastatin or simvastatin involves lactonisation of the intermediate 3,5-dihydroxy acid derivative or its salt either in the presence or absence of an acid catalyst as disclosed in the following documents:

i) U.S. Pat. No. 4,231,938 discloses a method for preparation of lovastatin by lactonisation of mevinolinic acid in refluxing ethyl acetate and in presence of a strong acid like hydrochloric acid.

ii) U.S. Pat. No. 4,444,784 discloses a method for lactonisation of the 3,5-dihydroxy pentanoic acid derivative by heating the reaction mixture with a dilute acid to give simvastatin (I). There is however no enabling disclosure about how the transformation is brought about and also there is no mention about the level of impurities formed during the lactonisation of the hydroxy acid.

iii) EP 0 877 742 teaches a method for lactonisation of mevinolinic acid present in a pre-treated fermentation broth by heating in a chlorinated solvent at pH 2.5-4.0 in the presence of a hydrochloric acid.

iv) U.S. Pat. No. 5,712,130 describes a method for lactonisation of mevinolinic acid by heating a acidified fermentation broth in butyl acetate at 40° C. to give lovastatin having purity of 90%.

v) U.S. Pat. No. 4,820,850 discloses a lactonisation method comprising of heating the simvastatin ammonium salt (II) in a hydrocarbon solvent such as toluene for 2-12 hours at 100° C., in the absence of an acid without disclosing the yield and purity.

vi) U.S. Pat. No. 4,916,239 claims and discloses a method for lactonisation of simvastatin ammonium salt comprising of agitating the ammonium salt (II) in a mixture of a water-miscible solvent, water and a acid catalyst at 20-30° C.

vii) U.S. Pat. No. 5,939,564 claims and discloses a method for lactonisation of the open ring 3,5-dihydroxy pentanoic acid derivative in the presence of a catalyst such as a salt of an organic base with an organic acid or inorganic acid like pyridine hydrobromide, pyridine hydrochloride or pyridine p-toluene sulfonate salt in a lower alkanol, ketone, ether, nitrile or mixture thereof (20-30 times dilution) at a temperature between ambient and 50° C.

viii) U.S. Pat. No. 5,917,058 A1 claims and discloses a method for preparation of simvastatin comprising lactonisation of the 3,5-dihydroxy pentanoic acid derivative in a weak acid such as acetic acid and in absence of a strong acid at a temperature below 55° C., and isolating simvastatin by addition of an anti-solvent such as water, hexane, heptane or cyclohexane.

ix) U.S. Pat. No. 6,562,984 describes a method for lactonisation in a solvent such as dichloromethane or acetonitrile and reagents such as methanesulfonic acid, phosphorous pentoxide, acidic ion exchange resin, molecular sieves, acidic clay, acidic silica gel and combinations thereof which binds water produced in a insoluble complex at a temperature not greater than 50° C., and preferably between 10-40° C.

x) U.S. Pat. No. 6,649,775 claims and discloses a process for lactonisation of 3,5-dihydroxy acid by refluxing in a inert organic solvent such as toluene and in the presence of large quantities (2 moles) of dehydrating agents like magnesium sulphate, sodium sulphate, calcium chloride, and molecular sieves for removal of water and shifting of equilibrium towards formation of the product.

xi) WO 02/094803 A1 claims and discloses a method for lactonisation of 3,5-dihydroxy pentanoic acid derivative or its ammonium salt in a mixture of acetonitrile and glacial acetic acid in anhydrous conditions at 65-70° C. and in the absence of a catalyst.

xii) WO 02/094804 A1 claims and discloses a method for lactonisation of simvastatin intermediate (II) comprising of heating in xylene at 135-140° C. for 20-30 minutes. The reaction is carried out in a very high dilution of 25-50 times and the dimer impurity (III) is formed in the range of 0.10 to 0.20% without any disclosure about the formation of other impurities.

xii) WO 02/00615 A2 describes a method for lactonisation of lovastatin by heating the broth with a mineral acid at 50-60° C., followed by extraction with a hydrophobic solvent such as toluene. Lactonisation is very slow requiring 20-60 hours and also the yield is quite low (54%).

xiii) US Application No. 2003/0109723 A1 discloses and claims a method for lactonisation of 3,5-dihydroxy pentanoic acid derivative or its ammonium salt comprising of refluxing the said hydroxy acid in a mixed organic solvent selected from toluene, ethyl acetate, isopropyl acetate, dichloromethane, chloroform, tetrahydrofuran and acetone, without an acid catalyst and under nitrogen sweep.

Lactonisation is carried out in a high dilution (40-50 times) of the solvent mixture.

Further, anti-hypercholestoremic drugs, such as atorvastatin, rosuvastatin and fluvastatin, which are prepared by the synthetic route also involve lactonisation of the 3,5-dihydroxy pentanoic acid derivative to give the corresponding 4-hydroxy pyran-2-one derivative, which is an intermediate of the above statin drugs.

U.S. Pat. No. 4,346,227 discloses a method for preparation of a pravastatin intermediate by cyclisation of the 3,5 dihydroxy acid in presence of a strong acid such as trifluoroacetic acid. This patent does not provide any enabling disclosure for the same.

U.S. Pat. No. 5,273,995 discloses a method for lactonisation of a substituted 3,5 dihydroxy atorvastatin derivative by refluxing in toluene in the presence of a strong acid like hydrochloric acid.

U.S. Pat. No. 4,739,073 discloses a method for lactonisation of a 3,5-dihydroxy derivative of fluvastatin wherein the reaction is carried out in the absence of an acid by refluxing in benzene.

From the above, it would be evident that all the methods disclosed in the prior art for synthesis of 4-hydroxy pyran-2-on derivatives (I) either involve heating 3,5-dihydroxy pentanoic acid derivative (II) in a organic solvent in presence or absence of an acid or carrying out the reaction at lower temperature in the presence of a strong acid such as methanesulfonic acid or in solvents such as acetic acid.

Lactonisation of the 3,5-dihydroxy pentanoic acid derivative or its salt (II) is invariably accompanied by the formation of associated impurities especially the dimer impurity (III), in variable amounts and which is difficult to remove utilizing conventional methods of purification and if removed, considerably lowers the yield of the product. The dimer impurity (III) is formed by reaction of the 3-hydroxy group of one molecule of compound (II) with the carboxyl group of another molecule of compound (II).

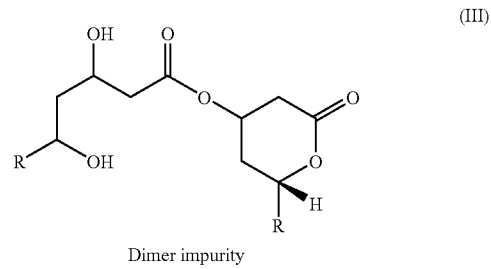

Dimer impurity

In summary, the prior art methods suffer from the following shortcomings:

i. These methods do not mention the level of impurities formed during lactonisation and also the yields obtained are generally low, thereby rendering these methods costly for commercial applications.

ii. Although, some of the methods, mention that the level of dimer impurity (III) is reduced below 0.1%, but there is absolutely no mention about other impurities such as anhydro (IV) and acetyl impurity (V), which could be formed when strong acids like methanesulfonic acid or a solvent like glacial acetic acid is employed.

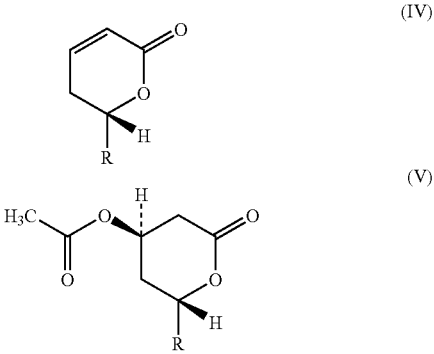

Compounds having the above impurities are difficult to purify, by conventional methods of purification and therefore, should be minimized at the reaction stage itself.

iii. The level of dilution utilized by the prior art methods is also very high viz. between 40-50 times (w/w) per gram of the starting compound, thus reducing the production capacity and increasing the time cycle for each run.

iv. Some of the methods require a long time between 20-60 hours for lactonisation, thereby reducing the production capacity commercially.

As the anti-hypercholestoremic drugs of formula (I) are valuable commercially and therapeutically, therefore, a need exists to synthesize these drugs having a 4-hydroxy pyran-2-one substituent in their structural formula by a method which not only reduces the level of impurities but also reduces reaction time, solvent dilution and gives compound (I) of high purity, substantially free from impurities.

The present inventors have found that 4-hydroxy pyran-2-one derivative (I) can be synthesized in a higher yield and purity through a highly selective method, comprising heating of 3,5-dihydroxy pentanoic acid derivative of formula (II) in a mixture of a aromatic hydrocarbon and a ketonic solvent at a temperature in the range of 60-92° C., which gives the object compound (I), a) in higher yield (63-78%).
b) of high purity above 99.5%.
c) substantially free from the dimer impurity (III) and other associated impurities such as the anhydro impurity (IV). There is no possibility of forming the acetyl impurity (V), since the present method does not utilize acetic acid or its derivatives.
d) in shorter reaction time of between 2.0 to 12.0 hours.

Further, it has been found that the reaction could be carried out using almost half the dilution of the solvent utilized in prior art methods. Significantly, the reaction could be carried out in the absence or presence of a weak acid like orthophosphoric acid. Both the conditions were found not to have any significant effect on the quality, formation of impurities etc.

Even though, various aromatic hydrocarbons and ketones could be used for conversion of compound (II) to (I), however the most optimum results were obtained when toluene and methyl ethyl ketone were used.

OBJECTS OF THE INVENTION

An object of the invention is to provide an improved process for preparation of 4-hydroxy pyran-2-one derivative of formula (I) of high purity, with dimer impurity of formula (III) less than 0.1% and anhydro impurity of formula (IV) less than 0.15%.

Another object of the invention is to provide a improved process for synthesis of 4-hydroxy pyran-2-one derivative of formula (I) by heating the corresponding 3,5-dihydroxy pentanoic acid derivative or its salt of formula (II) in a mixture of a aromatic hydrocarbon and a ketone and in presence or absence of a weak acid like orthophosphoric acid or its alkali dihydrogen salt or alkali hydrogen salt of dibasic acid and at a temperature between 60-92° C. and in a in a short duration of 2.0 to 12.0 hours as compared to between 20-60 hours reported in prior art methods.

Yet, another object of the invention relates to carrying out the lactonisation of the compound of formula (II) in a significantly lower dilution of the solvent mixture between 13 to 17 times (w/w) per gram of compound (II) giving compound (I) of high purity and thereby making the process cost-effective.

SUMMARY OF THE INVENTION

According to the main aspect of the present invention there is provided a process for preparation of a compound of formula (I),

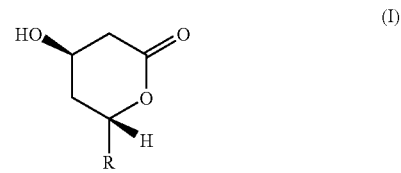

wherein R is,

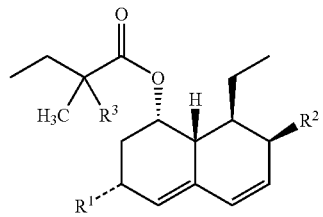

and wherein $R^1$ and $R^2$ are methyl and $R^3$ is hydrogen or methyl, comprising the steps of, heating a compound of formula (II),

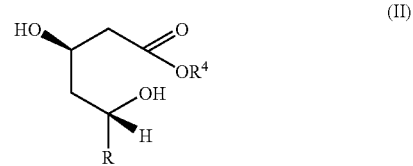

wherein R is as defined before, and $R^4$ is hydrogen, $NH_4^+$ or an alkali metal, in a solvent mixture consisting of an aromatic hydrocarbon and a ketone in an inert atmosphere at a temperature of between 60° C. to 92° C. in the absence or presence of orthophosphoric acid or its alkali dihydrogen salts or alkali hydrogen salts of a dibasic acid, followed by optional neutralization of the reaction mixture with an organic base and obtaining compound of formula (I) in high purity and substantially free of impurities through a step of isolation and crystallization.

DETAILED DESCRIPTION OF THE INVENTION

The present inventors have found that 4-hydroxy pyran-2-one derivative (I) can be synthesized from the 3,5-dihydroxy pentanoic acid derivative or its salt (II) by heating in a mixture of an aromatic hydrocarbon and a ketone in a period of 2.0-12.0 hours, optionally in the presence of a weak acid like orthophosphoric acid or its alkali dihydrogen salt or a alkali hydrogen salt of a dibasic acid to give compound (I), of high purity, with dimer impurity (III) below 0.1% and anhydro impurity (IV) below 0.15%, and which conforms to pharmacopoeial specification.

One aspect of the present invention provides a simple, efficient, cost effective method for manufacture of 4-hydroxy pyran-2-one derivatives of formula (I) of high purity substantially free from impurities.

Another aspect of the invention provides a method for manufacture of 4-hydroxy pyran-2-one derivatives of formula (I) by heating the corresponding 3,5-dihydroxy pentanoic acid derivative or its salt of formula (II) in a mixture of an aromatic hydrocarbon and a ketone in a ratio of 7:3.

Yet another aspect of the invention provides a method for manufacture of 4-hydroxy pyran-2-one derivatives of formula (I) by heating the corresponding 3,5-dihydroxy pentanoic acid derivative or its salt of formula (II) in a mixture of a toluene and methyl ethyl ketone.

A further aspect of the invention relates to a method comprising of heating the compound (II) or its salt in the presence or absence of a weak acid like orthophosphoric acid or its alkali dihydrogen salt or alkali hydrogen salt of a dibasic acid.

Yet a further aspect of the invention relates to a method for carrying out the lactonisation in a very low dilution between 13 to 17 times of the solvent mixture, at a temperature of 60-92° C., in a short time of 2.0 to 12.0 hours followed by evaporation of the solvent mixture and isolating the product of formula (I) from a hydrophobic solvent.

Yet another aspect of the invention relates to a method for purification of compound (I) by refluxing in a hydrophobic solvent and filtering the cooled mixture, followed by recrystallisation of compound (I) from a mixture of a water-miscible solvent and water to give compound (I) of high purity, having dimer impurity less than 0.1%, anhydro impurity less than 0.15 and conforming to pharmacopoeial specifications.

The selection of the solvent combination, ratio of the solvent mixture, dilution of the solvents, reaction temperature, and the absence or presence of a weak acid such as orthophosphoric acid or its alkali dihydrogen salts in providing 4-hydroxy-pyran-2-one derivatives of formula (I) of high purity with dimer impurity (III) less than 0.1% and anhydro impurity (IV) below 0.15%, forms the basis of the invention.

The method of manufacture of 4-hydroxy pyran-2-one (I) as per the present invention is summarized in Scheme-I for ready reference.

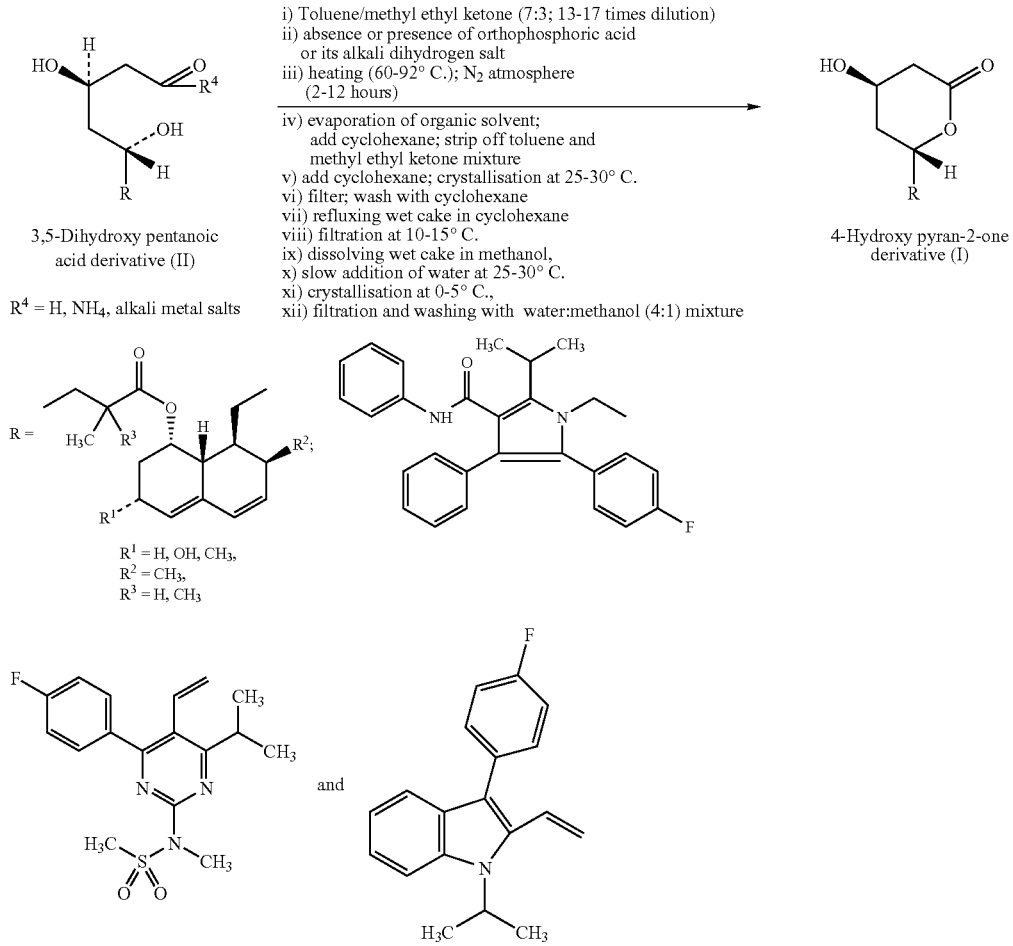

Scheme-1: Method for preparation of 4-hydroxy pyran-2-one derivative (I) as described in the present invention All the lactonisation experiments illustrated hereafter are all carried out on the corresponding 3,5-dihydroxy pentanoic acid derivative or salt of simvastatin (II).

A. Lactonisation of 3,5-Dihydroxy Pentanoic Acid Derivatives of Formula (I).

The lactonisation of 3,5-dihydroxy pentanoic acid derivative of formula (II) to give 4-hydroxy pyran-2-one derivative of formula (I) was found to depend on the following parameters:
  i) selection of the solvent mixture and their ratio,
  ii) dilution of the solvent,
  iii) reaction temperature,
  iv) selection of proton donors for promoting lactonisation.

i) Selection of the Solvent Mixture and Their Ratios.

Several solvents selected from aromatic hydrocarbons, ketones, and aliphatic hydrocarbons as mixtures were tried out in equal proportions to find out the solvent medium, which would minimise impurities such as dimer (III) and anhydro (IV) and give higher conversion of the product (I).

Aromatic hydrocarbons were selected from benzene, toluene, xylene but preferably toluene; ketones were selected from acetone, methyl ethyl ketone, methyl isobutyl ketone, and aliphatic hydrocarbons were selected from hexane, and cyclohexane but preferably cyclohexane.

The results obtained utilizing the above solvents in equal proportion are summarized in Table-I.

TABLE I

Comparison of various solvent mixtures in terms of conversion, impurity formation at reflux temperature in a solvent dilution of 17 times (w/w) per gram of the starting material

| No. | (1:1)(w/w) Ratio of various solvent mixtures | Reaction Time (hrs) | Product Conversion (%) | Level of impurities in reaction (%) Dimer (III) | Anhydro (IV) |
|---|---|---|---|---|---|
| 1. | Toluene/acetone | 46.0 | 91.95 | 0.65 | 0.41 |
| 2. | Toluene/methyl ethyl ketone | 35.0 | 93.0 | 0.26 | 0.41 |
| 3. | Methyl isobutyl ketone/methyl ethyl ketone | 18.0 | 94.84 | 0.14 | 0.86 |
| 4. | Cyclohexane/methyl ethyl ketone | 9.0 | 86.5 | 0.6 | 0.8 |

It is evident from the above data that among all these combinations, toluene/methyl ketone was found to be better than the others, as
  i) it had a lower impurity formation, although the reaction time was higher than the other combinations except toluene/acetone.
  ii) methyl ethyl ketone has a lower boiling point than the other solvents therefore, evaporation of the solvent is easier during isolation of the product as compared to other solvents.

Based on the result shown in Table-I, the inventors tried to see whether a change in the weight ratio of the solvent mixture from (1:1) ratio of toluene and methyl ethyl ketone would have any effect on the conversion of product (I) and impurity profile of the reaction. It was indeed found that changing the ratio of the toluene/methyl ethyl ketone mixture from (1:1) to (7:3) greatly increased the reaction rate, with reaction completing in only 12 hours which is much faster than (1:1) ratio, thereby considerably reducing the time for each run.

The results are summarized in Table-II, which shows the effect of different weight ratios of toluene/methyl ethyl ketone on reaction rate, conversion of 4-hydroxy pyran-2-one, and formation of impurities.

TABLE II

Comparison of results obtained with different ratios of toluene/methyl ethyl ketone solvent mixture (in absence of acid) at reflux temperature

| No. | Ratio of toluene/methyl ethyl ketone. | Reaction time(hrs) | Product conversion (%) | Level of impurities during reaction (%) Dimer (III) | Anhydro (IV) | Level of impurities in the isolated product (I) |
|---|---|---|---|---|---|---|
| 1. | 1:1 | 35.0 | 93.00 | 0.26 | 0.41 | Product purity between 99-100%. |
| 2. | 3:1 | 6.0 | 94.85 | 0.46 | 0.60 | Individual impurities less than 0.15% and dimer |
| 3. | 7:3 | 12.0 | 92.85 | 0.20 | 0.41 | impurity less than 0.1% |
| 4. | 3:7 | 45.0 | 89.63 | 0.68 | 0.78 | |

Lactonisation utilising the (7:3) combination of toluene and methyl ethyl ketone was extrapolated to other ketones to observe the effect on conversion, formation of impurities and reaction time.

The results obtained in the study are summarized in Table-III

TABLE III

Lactonisation of 4-hydroxy-pyran-2-ones utilising various combinations of toluene with ketones (absence of orthophosphoric acid or its dihydrogen salt) in a weight 7:3 ratio at reflux temperature.

| No. | Ketone utilised in combination with toluene | Reaction Time(hrs) | Conversion (%) | Impurities Dimer (%) | Anhydro (%) | Purity and level of impurities in the product (I). |
|---|---|---|---|---|---|---|
| 1. | Methyl ethyl ketone | 12.0 | 92.85 | 0.20 | 0.41 | Purity between 99-100%. Individual impurities below 0.15% and dimer impurity (III) less than 0.1%. |
| 2. | Methyl isobutyl ketone | 4.0 | 93.7 | 0.35 | 0.56 | |
| 3. | Cyclohexanone | 6.5 | 93.82 | 0.29 | 0.46 | |

Methyl ethyl ketone was found to be a better co-solvent as compared to the other ketones since impurity formation was comparatively lower, and also since it has a lower boiling point as compared to methyl isobutyl ketone and cyclohexanone, therefore evaporation of methyl ethyl ketone is much easier during isolation of the product.

ii) Dilution of the Toluene/Methyl Ethyl Ketone Mixture Per Gram of the 3,5-Dihydroxy Pentanoic Acid Derivative or its Ammonium Salt(II).

It is known from prior art methods that solvent dilution plays a major role in the formation of the dimer impurity (III). Methods reported in the prior art reveal that the dimer impurity (III) is usually formed when the dilution of the solvent medium is low. Large solvent dilution reduces the formation of dimer impurity (III) while lower dilution increases the formation of the dimer impurity (III). Reported methods point out to the utilisation of a very high dilution between 40-50 times of the solvent as reaction medium for minimizing dimer impurity (III).

The present inventors have surprisingly found that with the present method, dimer impurity (III) can be controlled even with a low dilution of the solvent mixture. Dilution of toluene/methyl ethyl ketone between 13.0 and 17.0 (w/w) per gram of the 3,5-dihydroxy pentanoic acid derivative was found to be optimum in minimizing the dimer impurity (III) along with associated impurities and which is summarized in Table-IV.

TABLE IV

Effect of solvent dilution on the conversion, formation of impurities, and reaction time during lactonisation of the 3,5-dihydroxypentanoic acid derivative (II) in toluene/methyl ethyl ketone (7:3)weight ratio and temperature of 80 ± 5° C.

| No. | Dilution of (7:3) toluene/methyl ethyl ketone (w/w) per gram of the starting material | Reaction Time (hrs) | Conversion of 4-hydroxy pyran-2-one (%) | Impurities (%) Dimer (III) | Anhydro (IV) |
|---|---|---|---|---|---|
| 1. | 25.0 | 13.0 | 92.41 | 0.21 | 0.40 |
| 2. | 17.0 | 12.0 | 92.85 | 0.20 | 0.41 |
| 3. | 13.0 | 14.0 | 92.30 | 0.27 | 0.38 |
| 4. | 4.0 | 5.5 | 92.24 | 1.23 | 1.48 |

It can be seen from the above data, that formation of the dimer impurity (III) is higher with a lower dilution of 4 times (w/w) per gram of the starting material and impurity formation was minimized for a dilution of 13.0 to 25.0 times of the solvent mixture (w/w) per gram of the starting compound.

Thus a dilution of between 13.0 and 17.0 times was found to be optimum for lactonisation which is in stark contrast to the high dilution between 40-50 times employed by prior art methods. The utilization of such low dilutions therefore makes the present method cost-effective.

iii) Reaction Temperature:

The inventors have studied the effect of temperature on lactonisation and found that at lower temperatures (below 50° C.) the reaction was slow, while at higher temperatures (60-90° C.), the reaction was faster. The results of the experiments carried out different dilutions of toluene/methyl ethyl ketone has been summarized in Table-V.

TABLE V

Effect of temperature on the reaction time, conversion, impurity formation during lactonisation of 3,5-dihydroxy pentanoic acid derivative or its salts (II) [in presence of orthophosphoric acid] in 17.0 times (w/w) dilution of the solvent.

| No. | Temperature | Reaction time | Conversion (%) | Impurity formation (%) Dimer (III) | Anhydro (IV) |
|---|---|---|---|---|---|
| 1. | 50° C. | 4.5 hours | 91.02 | 0.21 | 0.48 |
| 2. | 65° C. | 4.0 hours | 92.12 | 0.20 | 0.45 |
| 3. | 70° C. | 3.0 hours | 93.28 | 0.28 | 0.50 |
| 4. | 80° C. | 2.0 hours | 96.11 | 0.40 | 0.64 |
| 5. | 90° C. | 0.5 hours | 93.90 | 0.44 | 0.57 |

From the above table, it is evident that lactonisation can be carried out at a temperature between 60-85° C., but preferably 80±2° C., wherein the reaction is fast and the conversion is higher.

iv) Selection of Proton Donors for Promoting Lactonisation:

Several reagents such as orthophosphoric acid and its salts like sodium dihydrogen phosphate, potassium dihydrogen phosphate, salts of dibasic acid like sodium hydrogen sulphate, potassium hydrogen sulphate, potassium hydrogen phthalate were tried out.

TABLE VI

Effect of proton donors on the reaction time, conversion of 4-hydroxy pyran-2-one(I), formation of impurities utilizing toluene/methyl ethyl ketone (7:3)(w/w) mixture at a temperature of 80° C.

| No. | Reagent | Reaction Time (hrs) | Conversion (%) | Formation of impurities (%) Dimer (III) | Formation of impurities (%) Anhydro (IV) |
|---|---|---|---|---|---|
| 1. | Orthophosphoric acid (88%) | 2.0 | 96.11 | 0.40 | 0.64 |
| 2. | Sodium dihydrogen phosphate | 7.5 | 93.41 | 0.23 | 0.47 |
| 3. | Potassium dihydrogen phosphate | 13.0 | 92.44 | 0.50 | 0.56 |
| 4. | Potassium hydrogen sulphate | 12.0 | 89.86 | 0.33 | 0.57 |
| 5. | Potassium hydrogen phthalate | 13.5 | 20.46 | 0.05 | 0.27 |

It can be seen from Table-VI that from the above reagents, orthophosphoric acid was found to be a better proton donor, since the conversion was higher, impurity formation was lower, and most important is the fact that the reaction was completed in a very short time of only 2.0 hours.

The pH of the reaction medium is 3.5, when orthophosphoric acid is used as compared to sodium dihydrogen phosphate (pH:4.5), potassium dihydrogen phosphate (pH4.6), potassium hydrogen sulphate (pH1.5) and potassium hydrogen phthalate (pH 4.5), which suggests that the process of lactonisation is fast at pH:3.5 as compared to other pH.

Lactonisation of 3,5-dihydroxy pentanoic acid derivative (II) was tried out in the presence of other ketones such as methyl isobutyl ketone, cyclohexanone and cyclopentanone. The results are summarized in Table-VII.

TABLE VII

Lactonisation of 4-hydroxy-pyran-2-ones utilising various combinations of toluene with ketones (presence of orthophosphoric acid) in a (7:3) weight ratio and temperature of 80° C.

| No. | Ketone utilised in (7:3)(w/w) combination with toluene | Reaction time(hrs) | Product conversion (%) | Impurities (reaction mixture) Dimer (%) | Impurities (reaction mixture) Anhydro (%) |
|---|---|---|---|---|---|
| 1. | Methyl ethyl ketone | 2.0 | 96.11 | 0.40 | 0.64 |
| 2. | Methyl isobutyl ketone | 3.0 | 96.73 | 1.04 | 0.76 |
| 3. | Cyclohexanone | 3.0 | 91.28 | 0.24 | 0.94 |
| 4. | Cyclopentanone | 4.0 | 88.65 | 1.15 | 0.63 |

The combination of toluene/methyl ketone was found to be superior to combination of toluene with other ketones as the reaction is faster, conversion is higher and also the impurity formation is much lower as compared to the other toluene combinations.

The reagents depicted in Table-VI, are employed in molar proportions of between 0.95 to 1.10 moles per mole of the 3,5-dihydroxy pentanoic acid intermediate but preferably between 1.0 and 1.05 mole equivalent.

B. Isolation and Purification of 4-Hydroxy Pyran-2-One Derivatives of Formula (I).

a. Isolation of Compound (I).

The reaction mixture is cooled to ambient temperature, quenched with water and optionally neutralized with an organic base such as triethyl amine.

The molar proportion of triethyl amine employed is between 1.0 to 1.10 moles per mole of compound (I) but preferably between 1.01 and 1.05 moles. The pH obtained is 7.5±0.2 after addition of triethyl amine [1.02 moles per mole of compound (II)].

The aqueous layer is separated and the organic layer is concentrated under reduced pressure to distil toluene/methyl ethyl ketone mixture.

A hydrophobic solvent preferably cyclohexane is added to the residue and the mixture is again distilled under reduced pressure to completely strip off toluene/methyl ethyl ketone mixture.

The amount of cyclohexane added is between 3.0 to 8.0 times weight per gram but preferably 5.0 times (w/w) of the compound (II).

Cyclohexane [5.0 times (w/w)] is again added to the syrupy residue and the mixture agitated for 30 minutes at ambient temperature for complete precipitation of compound (I). Compound (I) is filtered and purified as such without drying.

b. Purification of Compound (I).

First Purification:

Wet cake of compound (I) obtained during isolation is added to a hydrophobic solvent preferably cyclohexane and refluxed for 15 minutes. The amount of cyclohexane added is between 15 and 25 times weight per gram of compound (II) but preferably 20 times (w/w) of compound (II).

The mixture is cooled to 10-15° C. and stirred for 120-150 minutes for complete crystallization of compound (I). The mixture is filtered and the wet cake washed with cyclohexane.

Second Purification:

The wet cake obtained in the first purification is dissolved in a water-miscible solvent selected from alkanol and a ketone but preferably an alkanol.

The alkanol is selected from methanol, ethanol, n-propanol, isopropanol but preferably methanol.

Compound (I) is dissolved in methanol. The quantity of methanol added is between 8.0 to 12.0 times weight per gram of compound (II), but preferably 10.0 times weight per gram of compound (II).

Butylated hydroxy toluene and butylated hydroxy anisole are added to the mixture. The amount of the anti-oxidant added is 0.005% weight/weight of compound (II).

The mixture is optionally treated with activated carbon and filtered. Water is added gradually to the filtrate. The volume of water added is between 10.0 and 15.0 times volume by weight of compound (II), but preferably 13.0 times volume/weight of compound (II). Water is added in 30-45 minutes at ambient temperature and stirred at 60-90 minutes for complete crystallization of compound (I). The mixture is filtered and washed with 25% aqueous methanol. The wet cake is dried at 40-45° C. under vacuum for 4.0 to 5.0 hours.

Compound (I) is obtained in a overall yield of between 63-70% for compound (Ib) viz. simvastatin and between 75-80% for compound (Ia) viz. lovastatin.

The purity of the 4-hydroxy pyran-2-one derivatives thus obtained is between 99.5% and 99.8% with dimer impurity (III) below 0.1% and anhydro impurity (IV) below 0.15%.

Lactonisation of 3,5-Dihydroxy Acid (II) in Presence of Orthophosphoric Acid:

In a specific embodiment, 3,5-dihydroxy pentanoic acid derivative (II) or its salt is added to a mixture of toluene [(12.0 parts w/w per part of compound (II)] and methyl ethyl ketone [5.0 parts w/w per part of compound (II). Nitrogen gas is bubbled into the reaction mixture, followed by addition of orthophosphoric acid [(1.05 mole equivalent per equivalent of compound (II)] at room temperature. The mixture is agitated at 80±2° C. for 2.0-2.5 hours with HPLC monitoring till the reaction proceeds to completion. The reaction mixture is cooled to 25-30° C. and diluted with water (2.0 times v/v). Triethyl amine [1.0 mole equivalent per mole of compound (II)] is added drop wise to the mixture and agitated for 15 minutes. The aqueous layer is separated and the organic layer is concentrated under reduced pressure. Cyclohexane [5 times w/w per gram of the compound (II)] is added to the syrupy residue and the solvent evaporated to completely strip off toluene and methyl ethyl ketone. Cyclohexane [5 times w/w per gram of the compound (II)] is added to the syrupy mass and the mixture agitated at 25-30° C. for complete crystallization of the lactone compound (I) containing 4-hydroxy pyran-2-one ring. Compound (I) is filtered and washed with cyclohexane.

The wet cake is added to cyclohexane under a nitrogen atmosphere and refluxed for 10-15 minutes. The mixture is allowed to cool between 25-30° C., and agitated mildly for 1.0 hour. The mixture is further cooled between 10-15° C. and stirred gently for 2.5 hours for complete crystallization of compound (I), which is then filtered and washed with cyclohexane.

The wet cake is then dissolved in methanol, to which butylated hydroxy toluene and butylated hydroxy anisole is added and after optional carbon treatment, the mixture is filtered and the carbon bed washed with methanol. The filtrate is cooled to 25-30° C. and water is added slowly to the filtrate for gradual crystallization of the pure compound (I), which is then filtered at 0-5° C. The wet cake is washed with methanol:water (1:4) and dried at 40-45° C.

Lactonisation of 3,5-Dihydroxy Acid (II) in Absence of Acid.

In a specific embodiment, 3,5-dihydroxy pentanoic acid derivative (II) or its salt is added to a mixture of toluene [(12.0 parts w/w per part of compound (II)] and methyl ethyl ketone [5.0 parts w/w per part of compound (II)]. Nitrogen gas is bubbled into the reaction mixture, and the mixture is agitated at 90±2° C. for 12.0-12.5 hours with HPLC monitoring till the reaction proceeds to completion. The reaction mixture is cooled to 25-30° C. and the solvent mixture is evaporated under reduced pressure. Cyclohexane [5 times v/v per gram of the compound (II)] is added to the syrupy residue and the solvent evaporated to completely strip off toluene and methyl ethyl ketone. Cyclohexane [5 times v/v per gram of the compound (II)] is added to the syrupy mass and the mixture agitated at 25-30° C. for complete crystallization of the lactone compound (I) containing 4-hydroxy pyran-2-one ring. Compound (I) is filtered and washed with cyclohexane.

The wet cake is added to cyclohexane under a nitrogen atmosphere and refluxed for 10-15 minutes. The mixture is allowed to cool between 25-30° C., and agitated mildly for 1.0 hour. The mixture is further cooled between 10-15° C. and stirred gently for 2.5 hours for complete crystallization of compound (I), which is then filtered and washed with cyclohexane.

The wet cake is dissolved in methanol, to which butylated hydroxy toluene and butylated hydroxy anisole is added and after optional carbon treatment, the mixture is filtered and the carbon bed is washed with methanol. The filtrate is cooled to 25-30° C. and water is added slowly to the filtrate for gradual crystallization of compound, which is then filtered at 0-5° C. The wet cake is washed with methanol:water (1:4) and dried at 40-45° C.

Compound (I) obtained by both the above methods (in presence of acid and absence of acid) has purity between 99.6 and 100%, with dimer impurity (III) below 0.1% and anhydro impurity (IV) below 0.15%.

Compound (I) prepared by this method conforms to pharmacopoeial specifications.

The invention is further illustrated by the following non-limiting examples.

Example 1

Preparation of 6(R)-[2-[8(S)-(2,2-dimethylbutyryloxy)-2 (S),6(R)-dimethyl-1,2,6,7,8,8a(R)-hexahydro-1(S)-napthyl]ethyl]-4(R)-hydroxy-3,4,5,6-tetrahydro-2H-pyran-2-one (Simvastatin) {in Presence of Orthophosphoric Acid}

Ammonium-7-[1,2,6,7,8,8a(R hexahydro-2(S),6(R)-dimethyl-8(S)-(2,2-dimethylbutyryloxy)-1(S)-naphthyl]-3(R),5(R)-dihydroxyheptanoate (Simvastatin ammonium salt) (100 gms; 0.22 moles) was added to a mixture of toluene (1400 ml) and methyl ethyl ketone (600 ml). Nitrogen gas was bubbled into the reaction mixture followed by drop wise addition of orthophosphoric acid (25.8 gms; 0.23 moles) at room temperature. The reaction mixture was agitated at 80±2° C., for 2.0-2.5 hours with HPLC monitoring. The reaction mixture was cooled to 20° C. and water (200 ml) followed by triethyl amine (22.29 gms; 0.22 moles) was added to the mixture. The aqueous layer was separated and the organic layer was distilled under reduced pressure to completely remove the solvent mixture. Cyclohexane (500 ml) was added and distilled again to completely strip off toluene/methyl ketone mixture. Cyclohexane (500 ml) was added to the syrupy mass and stirred for 30 minutes for complete crystallization of the product. The product was filtered and washed with cyclohexane (100 ml).

The wet cake was added to cyclohexane (2000 ml) and refluxed for 10-15 minutes. The mixture was gradually cooled to 25-30° C. and stirred for 3.0 hours. The mixture was cooled to 10-15° C. and filtered. The wet cake was washed with cyclohexane.

The wet cake obtained was dissolved in methanol (1000 ml). Butylated hydroxy toluene (5 mgms) and butylated hydroxy anisole (5 mgms) were added to the mixture and after optional carbon treatment was filtered and cooled to 25-30° C. Water was added gradually to the filtrate in 45 minutes and cooled to 0-5° C. The mixture was agitated at same temperature for 90 minutes and filtered. The wet cake was washed with a (4:1) mixture of water:methanol (200 ml). The wet cake was dried at 40-45° C. Yield: 62.56 gms; % Yield: 67.3; Purity: 99.7%.

Example-2

Preparation of 6(R)-[2-[8(S)-(2,2-dimethylbutyryloxy)-2(S),6(R)-dimethyl-1,2,6,7,8,8a(R)-hexahydro-1(S)-napthyl]ethyl]-4(R)-hydroxy-3,4,5,6-tetrahydro-2H-pyran-2-one (Simvastatin) {in Absence of Orthophosphoric Acid}

Ammonium-7-[1,2,6,7,8,8a (R)-hexahydro-2(S),6(R)-dimethyl-8(S)-(2,2-dimethylbutyryloxy)-1(S)-naphthyl]-3 (R),5(R)-dihydroxyheptanoate (Simvastatin ammonium salt) (100 gms; 0.22 moles) was added to a mixture of toluene (1400 ml) and methyl ethyl ketone (600 ml). Nitrogen gas was bubbled into the reaction mixture and the reaction mixture agitated at 90±2° C., for 12.0-12.5 hours with HPLC monitoring. The reaction mixture was cooled to 20° C. and distilled under reduced pressure to completely remove the solvent mixture. Cyclohexane (500 ml) was added and distilled again to completely strip off toluene/methyl ketone mixture. Cyclohexane (500 ml) was added to the syrupy mass and stirred for 30 minutes for complete crystallization of the product. The product was filtered and washed with cyclohexane (100 ml).

The wet cake was added to cyclohexane (2000 ml) and refluxed for 10-15 minutes. The mixture was gradually cooled to 25-30° C. and stirred for 3.0 hours. The mixture was cooled to 10-15° C. and filtered. The wet cake was washed with cyclohexane.

The wet cake obtained was dissolved in methanol (1000 ml). Butylated hydroxy toluene (5 mgms) and butylated hydroxy anisole (5 mgms) was added to the mixture and after optional carbon treatment was filtered, the carbon bed washed with methanol (200 ml) and cooled to 25-30° C. Water was added gradually to the filtrate in 45 minutes and cooled to 0-5° C. The mixture was agitated at same temperature for 90 minutes and filtered. The wet cake was washed with a (4:1) mixture of water:methanol (200 ml). The wet cake was dried at 40-45° C. Yield: 70.2 gms; % Yield: 70%; Purity: 99.71%.

Example-3

Preparation of [1S-[1α(R*),3 α,7β,8β(2S*,4S*),8a, β]]-2-methylbutanoic acid 1,2,3,7,8,8a-hexahydro-3, 7-dimethyl-8-[2-(tetrahydro-4-hydroxy-6-oxo-2H-pyran-2-yl)ethyl]-1-naphthalenyl ester (Lovastatin) {in Presence of Orthophosphoric Acid}

Ammonium-7-[1,2,6,7,8,8a(R-hexahydro-2(S),6(R)-dimethyl-8(S)-(2-methylbutyryloxy)-1(S)-naphthyl]-3(R),5(R)-dihydroxyheptanoate (lovastatin ammonium salt) (10 gms; 0.023 moles) was added to a mixture of toluene (140 ml) and methyl ethyl ketone (60 ml). Nitrogen gas was bubbled into the reaction mixture followed by drop wise addition of orthophosphoric acid (2.4 gms; 0.24 moles) at room temperature. The reaction mixture was agitated at 80±2° C., for 2.0-2.5 hours with HPLC monitoring. The reaction mixture was cooled to 20° C. and water (20 ml) followed by triethyl amine (2.3 gms; 0.023 moles) was added to the mixture. The aqueous layer was separated and the organic layer was distilled under reduced pressure to completely evaporate the solvent mixture. Cyclohexane (50 ml) was added and distilled again to completely strip off toluene/methyl ketone mixture. Cyclohexane (50 ml) was added to the syrupy mass and stirred for 30 minutes for complete crystallization of the product. The product was filtered and washed with cyclohexane (10 ml).

The wet cake was added to cyclohexane (200 ml) and refluxed for 10-15 minutes. The mixture was gradually cooled to 25-30° C. and stirred for 3.0 hours. The mixture was cooled to 10-15° C. and filtered. The wet cake was washed with cyclohexane.

The wet cake obtained was dissolved in methanol (1000 ml). Butylated hydroxy toluene (0.5 mgms) and butylated hydroxy anisole (0.5 mgms) was added to the mixture and after optional carbon treatment was filtered and cooled to 25-30° C. Water was added gradually to the filtrate in 45 minutes and cooled to 0-5° C. The mixture was agitated at same temperature for 90 minutes and filtered. The wet cake was washed with a (4:1) mixture of water:methanol (200 ml). The wet cake was dried at 40-45° C. Yield: 7.2 gms; % Yield: 78.2; Purity: 99.7%.

Example-4

Preparation of 6(R)-[2-[8(S)-(2,2-dimethylbutyryloxy)-2 (S),6(R)-dimethyl-1,2,6,7,8,8a(R)-hexahydro-1(S)-napthyl]ethyl]-4(R)-hydroxy-3,4,5,6-tetrahydro-2H-pyran-2-one (Simvastatin) {in Presence of Sodium Dihydrogen Phosphate}

Ammonium-7-[1,2,6,7,8,8a(R-hexahydro-2(S),6(R)-dimethyl-8(S)-(2,2-dimethylbutyryloxy)-1(S)-naphthyl]-3(R),5 (R)-dihydroxyheptanoate (Simvastatin ammonium salt) (10 gms; 0.022 moles) was added to a mixture of toluene (140 ml) and methyl ethyl ketone (60 ml). Nitrogen gas was bubbled into the reaction mixture followed by addition of sodium dihydrogen phosphate (25.8 gms; 0.23 moles) at room temperature. The reaction mixture was agitated at 80±2° C., for 7.5-8.0 hours with HPLC monitoring. The reaction mixture was cooled to 20° C. and water (200 ml). The reaction mixture was distilled under reduced pressure to completely remove the solvent mixture. Cyclohexane (500 ml) was added and distilled again to completely strip off toluene/methyl ketone mixture. Cyclohexane (500 ml) was added to the syrupy mass and stirred for 30 minutes for complete crystallization of the product. The product was filtered and washed with cyclohexane (100 ml).

The wet cake was added to cyclohexane (2000 ml) and refluxed for 10-15 minutes. The mixture was gradually cooled to 25-30° C. and stirred for 3.0 hours. The mixture was cooled to 10-15° C. and filtered. The wet cake was washed with cyclohexane.

The wet cake obtained was dissolved in methanol (100 ml). Butylated hydroxy toluene (0.5 mgms) and butylated hydroxy anisole (0.5 mgms) was added to the mixture and after optional carbon treatment was filtered and cooled to 25-30° C. Water was added gradually to the filtrate in 45 minutes and cooled to 0-5° C. The mixture was agitated at same temperature for 90 minutes and filtered. The wet cake was washed with a (4:1) mixture of water:methanol (200 ml). The wet cake was dried at 40-45° C. Yield: 6.3 gms; % Yield: 67.3%; Purity: 99.7%.

The invention claimed is:
1. A process for preparation of a compound of formula (I),

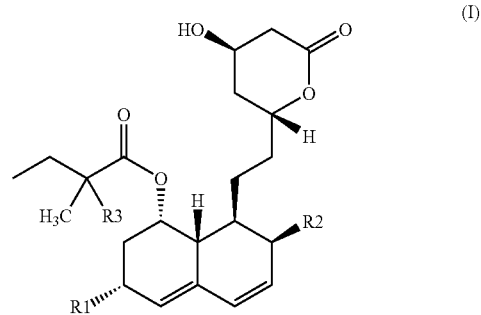

(I)

wherein $R^1$ and $R^2$ are methyl and $R^3$ is hydrogen or methyl, comprising the steps of,
heating a compound of formula (II),

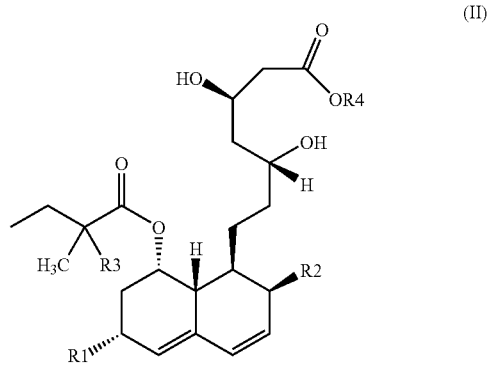

(II)

wherein R⁴ is hydrogen, $NH_4^+$ or an alkali metal,
    in a solvent mixture consisting of toluene and methyl ethyl ketone in an inert atmosphere at a temperature between 60-85° C. and optionally in the presence of orthophosphoric acid or its alkali dihydrogen salts or alkali hydrogen salts of a dibasic acid, followed by optional neutralization of the reaction mixture with an organic base and obtaining compound of formula (I) in high purity and substantially free of impurities through a step of isolation and crystallization.

2. A process according to claim 1, wherein the ratio of toluene and methyl ethyl ketone is between 8:2 and 2:8 (w/w).

3. A process according to claim 1, wherein the proportion of the solvent mixture to the substrate is between 13 and 17 times (w/w) per gram of compound (II).

4. A process according to claim 1, wherein orthophosphoric acid is employed in molar proportion of 1.0 mole to 1.2 moles per mole of compound (II).

5. A process according to claim 1, wherein the alkali dihydrogen salts of orthophosphoric acid are selected from sodium dihydrogen phosphate and potassium dihydrogen phosphate.

6. A process according to claim 1, wherein the molar proportion of alkali dihydrogen salt of orthophosphoric acid employed is 1.0 mole to 1.2 moles per mole of compound (II).

7. A process according to claim 1 wherein the alkali hydrogen salts of the dibasic acid are selected from potassium hydrogen sulphate and sodium hydrogen sulphate.

8. A process according to claim 7, wherein the molar proportion of the alkali hydrogen salt of the dibasic acid is 1.0 mole to 1.2 moles per mole of compound (II).

9. A process according to claim 1, wherein the organic base is triethyl amine.

10. A process according to claim 1, wherein the step of isolation comprises:
    i) evaporation of the solvent mixture,
    ii) addition of a hydrophobic solvent to the residue and evaporation of the solvent,
    iii) dissolution of the residue in a hydrophobic solvent, cooling to ambient temperature followed by collection of compound of formula (I) by filtration.

11. A process according to claim 10, wherein the hydrophobic solvent is cyclohexane.

12. A process according to claim 1, wherein the step of crystallization comprises:
    i) dissolution of compound (I) in a water-miscible solvent,
    ii) addition of water to the mixture, followed by crystallization of compound (I) and cooling between 0° C. and 5° C., and
    iii) collecting the filtered compound (I) in high purity by filtration.

13. A process according to claim 12, wherein the water-miscible solvent is alkanol.

14. A process according to claim 13, wherein the alkanol is methanol.

15. A process according to claim 1, wherein the ratio of toluene and methyl ethyl ketone is 7:3 (w/w).

* * * * *